United States Patent [19]

Fischer et al.

[11] Patent Number: 4,599,458

[45] Date of Patent: Jul. 8, 1986

[54] PREPARATION OF 2-METHYLALK-2-ENALS

[75] Inventors: Rolf Fischer, Heidelberg; Wolfgang Hoelderich, Frankenthal; Franz Merger, Frankenthal; Wolf D. Mross, Frankenthal; Hans-Martin Weitz, Bad Durkheim, all of Fed. Rep. of Germany

[73] Assignee: BASF Aktiengesellschaft, Ludwigshafen, Fed. Rep. of Germany

[21] Appl. No.: 742,200

[22] Filed: Jun. 7, 1985

[30] Foreign Application Priority Data

Jun. 12, 1984 [DE] Fed. Rep. of Germany ....... 3421809

[51] Int. Cl.$^4$ .............................................. C07C 45/61
[52] U.S. Cl. ..................................... 568/450
[58] Field of Search ......................... 568/450

[56] References Cited

U.S. PATENT DOCUMENTS

| 4,124,619 | 11/1978 | Fitton et al. | 260/410.6 |
| 4,192,820 | 3/1980 | Meissner et al. | 568/450 |
| 4,307,252 | 12/1981 | Weber et al. | 568/450 |

FOREIGN PATENT DOCUMENTS

| 2621224 | 12/1976 | Fed. Rep. of Germany ... 260/410.6 |
| 0113725 | 9/1981 | Japan ................................. 568/450 |
| 302331 | 6/1971 | U.S.S.R. ............................. 568/450 |

OTHER PUBLICATIONS

Liebigs Ann. 494 (1932), p. 273.
Zn. Org. Khim. 5 (1969), 1183, (English Translation).

Primary Examiner—Werren B. Lone
Attorney, Agent, or Firm—John H. Shurtleff

[57] ABSTRACT

2-Methylalk-2-enals of the formula

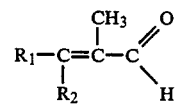

where $R^1$ and $R^2$ are each hydrogen, alkyl or an aromatic radical, are prepared by isomerization of an acrolein derivative of the formula

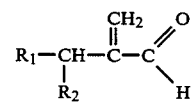

with a zeolite catalyst, an aluminum silicate and/or an aluminum phosphate.

7 Claims, No Drawings

PREPARATION OF 2-METHYLALK-2-ENALS

The present invention relates to a process for the preparation of 2-methylalk-2-enals by isomerization of acrolein derivatives over zeolite catalysts.

German Laid-Open Application DOS 2,621,224 discloses that 4-acetoxy-2-formylbut-2-ene (4-acetoxytiglaldenhyde) is obtained if hydrogen is passed, at elevated temperatures, through a solution of 4-acetoxy-2-formylbut-1-ene in which a sulfur-doped supported palladium catalyst is suspended. Mixtures of 4-acetoxy-2-formylbut-2-ene and 4-acetoxy-2-formylbutane in a ratio of four: one are isolated. This isomerization over a palladium catalyst has the disadvantage that substantial amounts of starting material are hydrogenated to the useless compound 4-acetoxy-2-formylbutane.

Liebigs Ann. 494 (1932), 273 describes the preparation of tiglaldehyde (trans-2-methylbut-2-enal) by treatment of x-ethylacrolein with calcium chloride, followed by distillation. This rearrangement reaction could not be confirmed when the procedure described in the literature was repeated.

2-Alkylacroleins can also be converted to the corresponding 2-methylalk-2-enals if the particular 2-alkylacrolein dialkylhydrazones are first prepared, these are then subjects to a rearrangement reaction with catalytic amounts strong acids to give the dialkylhydrazones of the corresponding 2-methylalk-2-enals, and finally the 2-methylalk-2-enals are liberated form the hydrazones by hydrolysis (Zh. Org. Khim. 5 (1969), 1183). Three reaction steps are therefore required. Moreover, the dialkylhydrazine employed is obtained in the form of a salt in the final reaction step and must therefore be liberated with an alkali, with formation of the neutral salt.

We have found that 2-methylalk-2-enals of the formula

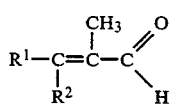

where $R^1$ and $R^2$ are each hydrogen, alkyl of 1 to 18 carbon atoms or an aromatic radical, can be prepared in a much more advantageous manner if an acrolein derivative of the formula

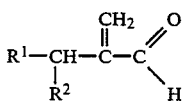

where $R^1$ and $R^2$ have the above meanings, is brought into contact with a zeolite catalyst, an aluminum silicate and/or an aluminum phosphate at from 30° to 450° C.

For example, for the isomerization of ethylacrolein to tiglaldehyde (trans-2-methylbut-2-enal), the process according to the invention can be represented by the following equation:

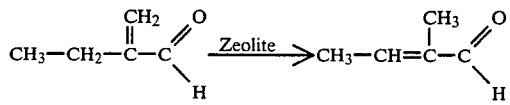

In the acrolein derivatives of the formula II which are used as starting materials, $R^1$ and $R^2$ are each hydrogen, alkyl of 1 to 18 carbon atoms or an aromatic radical. Examples of alkyl radicals are methyl, ethyl, n-propyl, isopropyl, n-butyl, isobutyl, tert.-butyl, pentyl, decyl and dodecyl. An example of a suitable aromatic radical is phenyl which is unsubstituted or substituted by other radicals, such as alkyl or alkoxy, or by halogen.

Examples of compounds of the formula II are 2-ethylacrolein, 2-n-butylacrolein, 2-isopropylacrolein, 2-n-propylacrolein, 2-decylacrolein, 2-n-pentylacrolein, 2-benzylacrolein, 2-heptylacrolein, 2-n-hexylacrolein, 2-isobutylacrolein and 2-n-nonylacrolein. The starting compounds of the formula II can be prepared by, for example, reacting an alkanal with formaldehyde and a secondary amine in the presence of a carboxylic acid (German Laid-Open Application DOS 3,106,557).

Examples of catalysts which are used for the novel isomerization of the acrolein derivatives II are zeolites. These are crystalline aluminosilicates which have a highly ordered structure with a rigid three-dimensional network of $SiO_4$ and $AlO_4$ tetrahedra connected by means of common oxygen atoms. The ratio of Si and Al atoms to oxygen is 1:2. The electrovalency of the aluminum-containing tetrahedra is compensated by inclusion of cations in the crystal, eg. an alkali metal or hydrogen ion. Cation exchange is possible. The spaces between the tetrahedra are occupied by water molecules prior to dehydration by drying or calcination. There are also crystalline compounds having a zeolite structure in which trivalent elements, such as B, Ga, Fe orCr, are incoprorated into the zeolite framework instead of the aluminum, or tetravalent elements, such as Ge, are incorporated instead of the silicone.

Preferably employed zeolites are those of the pentasil type, which may have different chemical compositions. These are aluminosilicate, borosilicate, ion silicate, gallium silicate, chromium silicate, arsenosilicate and bismuth silicate zeolites or mixtures of these, and aluminogermanate, borogermanate, gallium germanate and iron germanate zeolites or mixtures of these.

The aluminosilicate, borosilicate and iron silicate zeolites of the pentasil type are particularly suitable. The aluminosilicate zeolite is prepared from an aluminum compound, preferably $Al(OH)_3$ or $Al_2(SO_4)_3$, and a silicone component, preferably highly disperse silica, in an aqueous amine solution, in particular in 1,6-hexanediamine, 1,3-propanediamine or triethylenetetramine solution, with or without the addition of an alkali metal or alkaline earth metal, at from 100° to 220° C., under autogenous pressure. The resulting aluminosilicate zeolites possess an $SiO_2/Al_2O_3$ ratio of from 10 to 40,000, depending on the amounts of starting materials chosen. Aluminosilicate zeolites of this type may also be synthesized in an ether medium, such as diethylene glycol diemthyl ether, in an alcoholic medium, such as methanol or butane-1,4-diol, or simply in water.

The borosilicate zeolite is synthesized at from 90° to 200° C. under autogenous pressure by reacting a boron compound, eg. $H_3BO_3$, with a silicon compound, preferably highly disperse silica, ikn an aqueous amine solution, in particular in 1,6-hexanediamine, 1,3-propanediamine or triethylenetetramine solution, with or without the addition of an alkali metal or alkaline earth metal. Such borosilicate zeolites can also be prepared by carrying out the reaction in solution in ether, eg. diethylene glycol dimethyl ether, or in alcoholic solution, eg. in hexane-1,6-diol, instead of in an aqueous amine solution. The iron silicate zeolite is obtained from an iron compound, preferably $Fe_2(SO_4)_3$, and a silicon compound, preferably highly disperse silica, in an aqueous amine solution, in particular 1,6-hexanediamine, with or without the addition of an alkali metal or alkaline earth metal, at 100°-220° C. under autogenous pressure.

The aluminosilicate, borosilicate and iron silicate zeolites prepared in this manner are isolated, dried at from 100° to 160° C., preferably 110° C., and calcined at from 450° to 550° C., preferably 500° C., after which they can be molded with a binder in a weight ratio of from 90:10 to 40:60 to give extrudates or tablets. Suitable binders are a large variety of aluminas, preferably boehmite, amorphous aluminosilcates having an $SiO_2/Al_2O_3$ ratio of from 25:75 to 95:5, preferably 75:25, silica, preferably highly disperse $SiO_2$, mixtures of highly disperse $SiO_2$ and highly disperse $Al_2O_3$, highly disperse $TiO_2$ and clay. After the molding procedure, the extrudates or tablets are dried at 110° C. for 16 hours and calcined at 500° C. for 16 hours. Advantageous catalysts are also obtained if the aluminoslicate or borosilicate zeolite isolated is molded directly after the drying procedure and only subjected to calcination after the molding procedure. However, the aluminosilicate, borosilicate and iron silicate zeolites can also be used in pure form as extrudates or tablets, without a binder.

It is also possible to use aluminosilicate zeolites of the Y type, which are prepared from silica sol (29% of $SiO_2$) and sodium aluminate in an aqueous medium. These aluminosilicate zeolites can likewise be molded with binders before being used. The zeolites of the mordenite type and of the X type are also useful.

If the synthesis produces the zeolite not in the catalytically active, acidic H form but in, for example, the Na form, the latter can be partially or completely converted to the desired H form by iron exchange with ammonium ions followed by calcination, or by treatment with an acid.

Since, when the zeolite catalysts are used according to the invention, deactivation can occur as a result of coking, it is preferable to regenerate the zeolites, by burning off the coke deposit with air or with an air/$N_2$ mixture at from 400° to 550° C., preferably 500° C. As a result of this procedure, the zeolites again attain their initial activity.

To increase the selectivity, the catalyst life and the number of regenerations, it may be useful to modify the zeolite catalysts. In a suitable method of modification, the unmolded or molded zeolite is doped with an alkali metal such as sodium, unless the alkali metal form of the zeolite is already obtained in the synthesis, with an alkaline earth metal such as Ca or Mg, or with an earth metal such as B or Tl, for example by ion exchange or by impregnation with the corresponding metal salts.

Particularly advantageous catalysts can be obtained by doping the zeolites with transition metals, such as W, Fe or Zn, with noble metals, such as Pd, or with rare earth metals, such as Ce or La. For example, the following procedure can be adopted: the molded pentasil zeolite is initially taken in a siphon tube, and, for example, an aqueous solution of a halide or nitrate of one of the above metals is passed over at from 20° to 100° C. Ion exchange of this type can be carried out on, for example, the hydrogen, ammonium and alkali metal forms of the zeolite. In another possible method of applying metals to the zeolite, the zeolite material is impregnated with, for example, a halide, a nitrate or an oxide of the above metals in aqueous or alcoholic solution. Both ion exchange and impregnation are followed by one or more drying procedures and, if required, further calcination.

In a possible method of modification, the extruded or unextruded zeolite is impregnated for a certain time (about 30 minutes) with a solution of tungstic acid ($H_2WO_4$) or $Ce(NO_3)_3.6 H_2O$. The supernatant solution is then freed from water in a rotary evaporator, and the impregnated zeolite is dried at about 150° C. and calcined at about 550° C. This impregnation process can be carried out several times in succession in order to obtain the desired metal content.

It is also possible, for example, to prepare an ammoniacal $Pd(NO_3)_2$ solution and to suspend the pure zeolite powder at 40°-100° C. for about 24 hours in this solution, while stirring. After filtration, drying at about 110° C. and calcination at about 500° C., the resulting zeolite material can be further processed with or without a binder to give extrudates or pellets.

Ion exchange with the H form of the zeolite can be carried out by initially taking the zeolite, in the form of extrudates or pellets, in a column, and circulating over it, for example, an ammoniacal $Pd(NO_3)_2$ solution at slightly elevated temperatures of from 30° to 80° C. for 15-20 hours. The product is then washed thoroughly with water, dried at about 150° C. and calcined at about 550° C.

For some metal-doped zeolites, after-treatment with hydrogen is advantageous. In another possible method of modification, the zeolite material, molded or unmolded, is treated with an acid, such as hydrochloric acid, hydrofluoric acid or phosphoric acid, and/or with steam. The activity of the catalyst can be set in respect of optimum selectivity of the desired reaction product by partial coking (precoke).

Aluminosilicates and/or aluminum phosphates can also be used as catalysts for the novel isomerization of the acrolein derivatives of the formula II.

Aluminosilicates are compounds of $Al_2O_3$ and $SiO_2$. Compounds of this type can be prepared from, for example, $Al_2(SO_4)_3. 18 H_2O$ and waterglass. The procedure is carried out, for example, by combining the $Al_2$-

($SO_4)_3 \cdot 18 H_2O$ and the waterglass at pH 1-3, preferably pH 1.5, in the presence of $H_2SO_4$, and then reacting this mixture with an ammonia solution at pH 4-8, preferably 6, at from 0° to 50° C., preferably from 20° to 30° C. The resulting precipitate is filtered off, washed with ammonium carbonate solution and dried at from 50° to 150° C. Particularly advantageous catalysts are obtained if the $SiO_2:Al_2O_3$ ratio is brought to 80:20-20:80, in particular 75:25-35:65.

Aluminophosphates can be synthesized by, for example, precipitation from $Al(NO_3)_3 \cdot 9 H_2O$ with $(NH_4)_3PO_4$, $(NH_4)_2HPO_4$ or $(NH_4)H_2PO_4$ at different pH, in particular from 3 to 10. The product is filtered off, washed, dried at from 50° to 150° C., preferably from 60° to 100° C., and calcined at from 300° to 900° C., preferably from 500° to 800° C. The aluminosilicates and aluminophosphates prepared in this manner can be processed and used in pure form, without a binder, to give extrudates, tablets or fluidizable material. However, after isolation, drying and possible calcination, they may also be processing with different binders to give extrudates or tablets. The weight ratio of silicate or phosphate to binder is advantageously from 90:10 to 30:70. Suitable binders are various aluminas, preferably boehmite, silica, preferably highly disperse $SiO_2$, mixtures of highly disperse $SiO_2$ and highly disperse $Al_2O_3$, highly disperse $TiO_2$ and clay. After the molding procedure, the extrudates or pellets are, for example, dried at 110° C. for 16 hours and calcined at 500° C. for 16 hours.

These catalysts, too, can be regenerated as described above when they become deactivated by coking. To increase the selectivity, the catalyst life and the number of regenerations, these catalysts too can be modified and doped, as stated above for the zeolites. The catalysts can be used alternatively in the form of, for example, 2-4 mm extrudates, tablets of 3-5 mm diameter or powders having a particle size of from 0.1 to 0.5 mm.

The acrolein derivatives of the formula II are brought into contact with the stated catalysts at from 30° to 500° C., the reaction advantageously being carried out in a trickle-bed reactor. However, it is also possible to use a stirred flask or a stirred autoclave as the reaction vessel. Isomerization is carried out, for example, in the gas phase at from 150° to 450° C., preferably fro 300° to 400° C. and at a space velocity (WHSV) of from 0.1 to 20, preferably from 0.5 to 5, $h^{-1}$ (g of acrolein compound II per g of catalyst per hour), but may furthermore be effected in the liquid phase at from 30° to 300° C.

The process can be carried out batchwise or continuously, under atmospheric or superatmospheric pressure. Unconverted starting materials of the formula II can, if required, be separated off from the resulting 2-methylalk-2-enals I by distillation after the reaction, and can be reused for the reaction according to the invention.

The isomerization can be effected in the presence of a gas, such as hydrogen, nitrogen or steam, and this influences the product composition and the catalyst life. In particular, deactivation of the catalyst can be suppressed by adding steam.

The 2-methylalk-2-enals I obtainable by the novel process are useful intermediates for the preparation of dyes, drugs and crop protection agents.

EXAMPLES 1 to 14

For the isomerization in the gas phase under isothermal conditions, ethylacrolein was passed over the catalyst in a tube reactor having an internal diameter of 0.6 cm and a length of 90 cm, at from 350° to 400° C., the experiment lasting about 6 hours in each case. The type of catalyst, the temperature selected, the space velocity (WHSV) and the selectivity are shown in the Table below.

| Example | 1 | 2 | 3 | 4 | 5 | 6 | 7 | 8 | 9 | 10 | 11 | 12 | 13 | 14 |
| --- | --- | --- | --- | --- | --- | --- | --- | --- | --- | --- | --- | --- | --- | --- |
| Catalyst | A | B | C | D | E | F | G | H | I | J | K | L | M | N |
| Temperature [°C.] | 350 | 400 | 400 | 400 | 400 | 400 | 400 | 400 | 400 | 400 | 400 | 400 | 400 | 400 |
| WHSV [$h^{-1}$] | 1.3 | 2.5 | 1.9 | 2 | 2 | 2 | 0.8 | 0.7 | 1.9 | 1.9 | 1.7 | 1.8 | 1.8 | 1.8 |
| Conversion [%] | 20.8 | 14.8 | 17.5 | 17.4 | 12.0 | 26.3 | 9.7 | 29.1 | 11.9 | 16.1 | 21.2 | 36 | 13.9 | 12.2 |
| Selectivity [%] Tiglaldehyde | 47.1 | 77.7 | 73.7 | 79.3 | 67.5 | 76.4 | 89.6 | 76.6 | 84.0 | 82.1 | 72.2 | 61.1 | 48.9 | 43.4 |

The reaction products obtained were worked up by distillation and characterized by their boiling points, refractive indices and NMR spectra. Quantitative determination of ethylacrolein and tiglaldehyde was carried out by gas chromatography. The catalysts used were prepared as described below.

CATALYST A

An aluminosilicate zeolite of the pentasil type was synthesized under hydrothermal conditions, under autogenous pressure and at 150° C., from 65 g of highly disperse $SiO_2$ and 20.3 g of $Al_2(SO_4)_3 \cdot 18 H_2O$ in 1 kg of an aqueous 1,6-hexanediamine solution (50:50 (w/w) mixture) in a stirred autoclave. The crystalline reaction product was filtered off, washed thoroughly, dried at 110° C. for 24 hours and calcined at 500° C. for 24 hours. This aluminosilicate zeolite contained 91.6% by weight of $SiO_2$ and 4.6% by weight of $Al_2O_3$. It was molded with boehmite in a weight ratio of 60:40 to give 2 mm extrudates, which were dried at 110° C. for 16 hours and calcined at 500° C. for 24 hours.

CATALYST B

A boron zeolite of the pentasil type was prepared by a hydrothermal synthesis from 64 g of highly disperse $SiO_2$, 12.2 g of $H_3BO_3$ and 800 g of an aqueous 1,6-hexanediamine solution (50:50 (w/w) mixture) at 170° C. under autogenous pressure in a stirred autoclave. The crystalline reaction product was filtered off, washed thoroughly, dried at 110° C. for 24 hours and calcined at 500° C. for 24 hours. This borosilicate zeolite contained 94.2% by weight of $SiO_2$ and 2.32% by weight of $B_2O_3$.

2 mm extrudates were prepared from this by molding with boehmite in a weight ratio of 60:40, and the extrudates were dried at 110° C. for 16 hours and calcined at 500° C. for 24 hours.

CATALYST C

This catalyst was prepared by molding an iron silicate zeolite with boehmite in a weight ratio of 60:40 to give extrudates and then calcining these at 500° C. for 16 hours. The iron silicate zeolite of the pentasil type was synthesized under hydrothermal conditions, under autogenous pressure and at 165° C., from 273 g of waterglass, dissolved in 253 g of an aqueous 1,6-hexanediamine solution (50:50 (w/w) mixture), and 31 g of iron sulfate, dissolved in 21 g of 96% strength sulfuric acid, and 425 g of water, in the course of 4 days in a stirred autoclave. The product was then filtered off, washed thoroughly, dried at 100° C. for 24 hours and calcined at 500° C. for 24 hours. This iron silicate zeolite had an $SiO_2/Fe_2O_3$ ratio of 17.7 and an $Na_2O$ content of 0.62% by weight.

CATALYST D

The catalyst was obtained from an NaY zeolite, which had been molded with boehmite in a ratio of 60:40, by ion exchange with $NH_4Cl$ at 80° C. and calcination at 500° C. The ammonium exchange followed by calcination was repeated several times until the residual sodium content was 0.21% by weight.

CATALYST E

The catalyst used was the commercially available zeolite ®Zeolon 900 (Norton Chemical Proces Products, U.S.A.), which was molded with silica in a ratio of 60:40 to give 2 mm extrudates.

CATALYST F

Catalyst B was impregnated with an aqueous saturated $H_2WO_4$ solution for about 30 minutes, and the water in the residual supernatant solution was stripped off in a rotary evaporator, after which the catalyst was dried at 130° C. and calcined at 550° C. The procedure was repeated until the catalyst had a W content of 4% by weight.

CATALYST G

Catalyst G was prepared similarly to catalyst F, except that $Ce(NO_3)_3.6 H_2O$ was used. Impregnation was carried out until the Ce content of the catalyst reached 7.2% by weight.

CATALYST H

An ammoniacal $Pd(NH_3)_4(NO_3)_2$ solution was circulated over catalyst B at a rate of 65 ml/min. The product was then dried at 110° C. and calcined at 500° C. The Pd content was 3.3% by weight.

CATALYST I

Catalyst B was subjected to ion exchange with a 20% strength NaCl solution at 80° C. After calcination at 500° C., the catalyst contained 0.28% by weight of Na.

CATALYST J

Catalyst B was impregnated with magnesium acetate for about 30 minutes, dried at 110° C. and calcined at 500° C. The Mg content wa 2.3% by weight.

CATALYST K

Catalyst C was subjected to ion exchange with a 20% strength $NH_4Cl$ solution at 80° C., and calcined at 500° C. The procedure was repeated several times until the catalyst contained only 0.03% by weight of Na.

CATALYST L

This catalyst was an aluminosilicate having an $SiO_2:Al_2O_3$ ratio of 75:25. It was prepared by combining 589 g of $Al_2(SO_4)_3.18 H_2O$ with 989 g of waterglass ($SiO_2$ content 27.3% by weight) in the presence of $H_2SO_4$ at pH 1.5, and then diluting the mixture with 1 l of water. The resulting solution and 677 g of ammonia solution were added simultaneously, but separately, to 2 l of water in a vessel in the course of 25 minutes at 20° C. and pH 6, while stirring. Stirring was continued for 1 hour, after which the precipitate formed was filtered off and washed thoroughly with 0.5% strength by weight $(NH_4)_2CO_3$ solution. The aluminosilicate, which had an ash content of 39.4 g/100 g, was tabletted and then dried at 110° C. for 16 hours.

CATALYST M

This catalyst was an aluminosilicate having an $SiO_2:Al_2O_3$ ratio of 35:65. It was prepared similarly to catalyst L, except that 153 g of $Al_2(SO_4)_3.18 H_2O$ and 461 g of waterglass were used.

CATALYST N

A solution of 262.5 g of $Al(NO_3)_3.9 H_2O$ in 400 ml of water was added to a solution of 80.5 g of $NH_4H_2PO_4$ in 300 ml of water in the course of one hour. During this procedure, ammonia solution was added dropwise to maintain a pH of 4. The resulting precipitate was stirred for a further 16 hours and then filtered off, washed thoroughly with 800 ml of water, dried at 60° C. for 16 hours and calcined at 750° C. for 3 hours to give a product which contained 22.6% by weight of Al and 23.9% by weight of P. The resulting aluminophosphate was pressed to 5 mm tablets, which were dried at 110° C. for 16 hours and calcined at 500° C. for 16 hours.

EXAMPLE 15

To determine the effects of the temperature on the conversion and the selectivity, Examples 2, 12 and 14 were repeated at the temperatures and space velocities stated in the Table below.

| Catalyst | B | B | B | L | L | N | N |
| --- | --- | --- | --- | --- | --- | --- | --- |
| Temperature [°C.] | 300 | 350 | 400 | 350 | 400 | 350 | 400 |
| WHSV [$h^{-1}$] | 0.8 | 0.8 | 0.8 | 1.8 | 1.8 | 1.8 | 1.8 |
| Conversion [%] | 20.6 | 27.8 | 47.8 | 28.2 | 36.0 | 7.0 | 12.2 |
| Selectivity [%] Tiglaldehyde | 30.6 | 52.5 | 63.8 | 38.7 | 61.1 | 48.6 | 43.4 |

EXAMPLE 16

To determine the effect of the change in space velocity on the product spectrum, Example 15 was carried out using catalyst B at a space velocity (WHSV) of 2.5. The results shown in the Table below were obtained, these being compared with Example 15.

| WHSV | 0.8 | 2.5 |
| --- | --- | --- |
| Conversion % | 47.8 | 14.8 |
| Selectivity % Tiglaldehyde | 63.8 | 77.7 |

We claim:

1. A process for the preparation of a 2-methylalk-2-enal of the formula

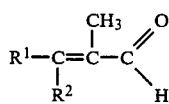  I where $R^1$ and $R^2$ are each hydrogen, alkyl of 1 to 18 carbon atoms, phenyl or phenyl substituted by alkyl, alkoxy or halogen, which process comprises:
bringing an acrolein derivative of the formula

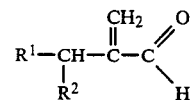  II where $R^1$ and $R^2$ have the above meanings, into contact with at least one catalyst selected from the group consisting of a zeolite, an aluminum silicate and an aluminum phosphate at from 30° to 500° C.

2. A process as claimed in claim 1, wherein the acrolein derivative used is ethylacrolein.

3. A process as claimed in claim 1, wherein zeolite of the pentasil type is used as the catalyst.

4. A process as claimed in claim 1, wherein an aluminosilicate zeolite is used as the catalyst.

5. A process as claimed in claim 1, wherein a borosilicate zeolite is used as the catalyst.

6. A process as claimed in claim 1, wherein an iron silicate zeolite is used as the catalyst.

7. A process as claimed in claim 1, wherein the catalyst used is an aluminosilicate zeolite of the Y type.

* * * * *